United States Patent
Baril et al.

(10) Patent No.: US 11,627,987 B2
(45) Date of Patent: Apr. 18, 2023

(54) LOW IMPACT CUTTING GUARD

(71) Applicant: Covidien LP, Mansfield, MA (US)

(72) Inventors: Jacob C. Baril, Norwalk, CT (US);
Saumya Banerjee, Hamden, CT (US);
Matthew A. Dinino, Newington, CT (US)

(73) Assignee: Covidien LP, Mansfield, MA (US)

( * ) Notice: Subject to any disclaimer, the term of this patent is extended or adjusted under 35 U.S.C. 154(b) by 72 days.

(21) Appl. No.: 16/879,709

(22) Filed: May 20, 2020

(65) Prior Publication Data

US 2021/0361321 A1 Nov. 25, 2021

(51) Int. Cl.
*A61B 17/34* (2006.01)
*A61B 90/00* (2016.01)

(52) U.S. Cl.
CPC ...... *A61B 17/3494* (2013.01); *A61B 17/3423* (2013.01); *A61B 2090/036* (2016.02); *A61B 2217/005* (2013.01)

(58) Field of Classification Search
CPC ............ A61B 17/3423; A61B 17/3494; A61B 2217/005; A61B 2218/008; A61B 2017/345; A61B 2017/3425; A61B 2017/3427; A61B 2017/3429; A61B 17/00234; A61B 17/3421; A61M 2039/0276; A61M 2039/0282; A61M 2039/0297; A61M 39/02; A61M 39/0247
USPC ......... 606/172; 128/856; 604/332, 334, 338; 600/208
See application file for complete search history.

(56) References Cited

U.S. PATENT DOCUMENTS

| | | | |
|---|---|---|---|
| 5,643,283 | A | 7/1997 | Younker |
| 6,059,793 | A | 5/2000 | Pagedas |
| 6,156,055 | A | 12/2000 | Ravenscroft |
| 6,162,209 | A | 12/2000 | Gobron et al. |
| 6,171,317 | B1 | 1/2001 | Jackson et al. |
| 6,206,889 | B1 | 3/2001 | Bennardo |
| 6,224,612 | B1 | 5/2001 | Bates et al. |
| 6,228,095 | B1 | 5/2001 | Dennis |
| 6,248,113 | B1 | 6/2001 | Fina |
| 6,258,102 | B1 | 7/2001 | Pagedas |
| 6,264,663 | B1 | 7/2001 | Cano |

(Continued)

FOREIGN PATENT DOCUMENTS

| | | |
|---|---|---|
| WO | 2004002334 A1 | 1/2004 |
| WO | 2014158880 A1 | 10/2014 |

*Primary Examiner* — Tan-Uyen T Ho
*Assistant Examiner* — Bridget E. Rabaglia
(74) *Attorney, Agent, or Firm* — Carter, DeLuca & Farrell LLP

(57) ABSTRACT

A tissue guard for use with a surgical access device includes a body having a proximal end, a distal end and lumen defined therebetween. A proximal lip extends radially from the proximal end and is configured to mount atop a rim of an access device. The proximal lip includes an annular channel defined therein disposed in fluid communication with the lumen, the annular channel configured to direct surgical gases from the lumen to a smoke evacuation system. The annular channel includes a neck defined therein disposed between the lumen and the annular channel, the neck having geometry configured to induce the evacuation of surgical gases or smoke therethrough. One or more fingers extend from the proximal lip and are configured to engage an access device to secure the tissue guard thereon.

20 Claims, 3 Drawing Sheets

(56) References Cited

U.S. PATENT DOCUMENTS

| | | |
|---|---|---|
| 6,270,505 B1 | 8/2001 | Yoshida et al. |
| 6,280,451 B1 | 8/2001 | Bates et al. |
| 6,344,026 B1 | 2/2002 | Burbank et al. |
| 6,350,266 B1 | 2/2002 | White et al. |
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,961,406 B2 * | 2/2015 | Ortiz ............... A61B 17/3462 600/204 |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,707,011 B2 * | 7/2017 | Malkowski ........ A61B 17/3423 |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2013/0053796 A1* | 2/2013 | Robinson ................ A61M 1/90 604/319 |
| 2013/0178710 A1* | 7/2013 | Suh .................... A61B 17/0293 600/205 |
| 2019/0110786 A1* | 4/2019 | Ip ........................... A61B 17/02 |
| 2021/0008325 A1* | 1/2021 | Spence ................. A61M 16/16 |

* cited by examiner

LOW IMPACT CUTTING GUARD

FIELD

The present disclosure relates to tissue specimen removal and, more particularly, to surgical access devices, tissue guards and systems incorporating the same for use in tissue specimen removal procedures and other surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically, a surgical sleeve and a specimen containment bag are used for this purpose. Moreover, during specimen rescission, smoke may cloud the operating site and may require evacuation therefrom. Smoke evacuation systems are commonplace for use with the surgical sleeve.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard for use with a surgical access device that includes a body including a proximal end, a distal end and lumen defined therebetween. A proximal lip extends radially from the proximal end and is configured to mount atop a rim of an access device. The proximal lip includes an annular channel defined therein disposed in fluid communication with the lumen, the annular channel configured to direct surgical gases from the lumen to a smoke evacuation system. The annular channel includes a neck defined therein disposed between the lumen and the annular channel, the neck having geometry configured to induce the evacuation of surgical gases therethrough. One or more fingers extends from the proximal lip and is configured to engage an access device to secure the tissue guard thereon.

In aspects according to the present disclosure, the proximal lip is bulbous to encourage engagement with the rim of the access device. In other aspects according to the present disclosure, the finger of the proximal lip includes a flange configured to engage an underside of the rim of the access device to facilitate engagement therewith.

In aspects according to the present disclosure, the proximal lip includes a connection disposed in fluid communication with the annular channel and extending perpendicularly from the proximal lip. In other aspects according to the present disclosure, the connection sits flush with the access device.

In aspects according to the present disclosure, the geometry of the neck induces a Venturi Effect from the lumen through to the annular channel.

In aspects according to the present disclosure, the geometry of the neck induces a vortex effect from the lumen through to the annular channel.

In aspects according to the present disclosure, the geometry of the neck is configured to maximize the flow of surgical gases therethrough.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

DETAILED DESCRIPTION

Figure 1A:
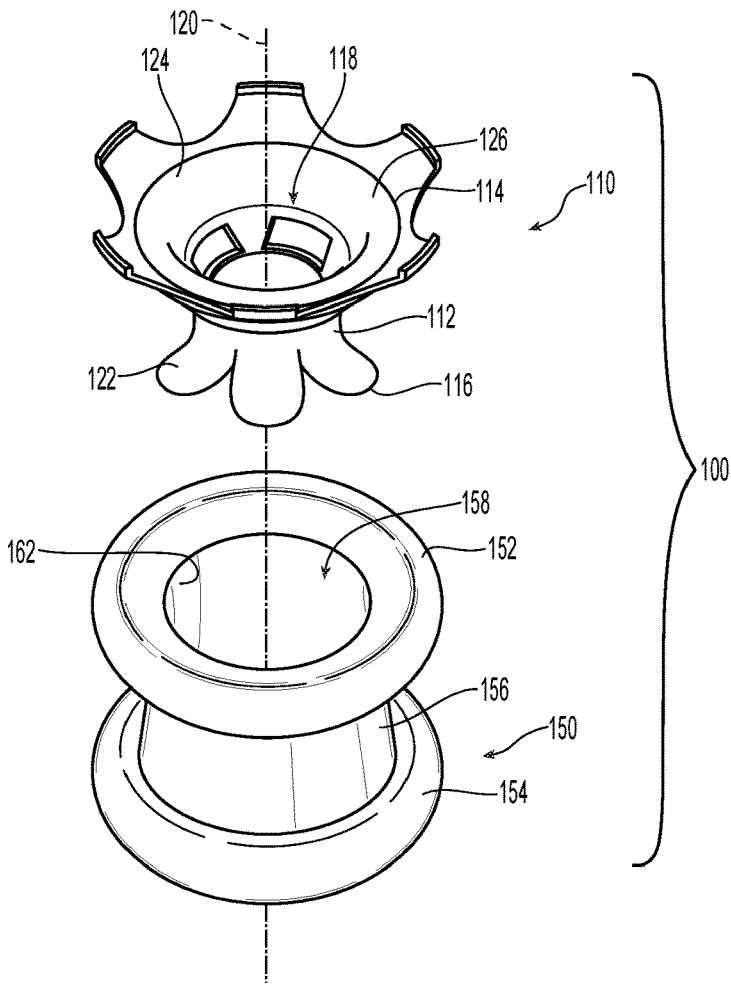
FIG. 1A is an exploded, top, perspective view of a prior art system including an access device and a tissue guard.
Figure 1B:
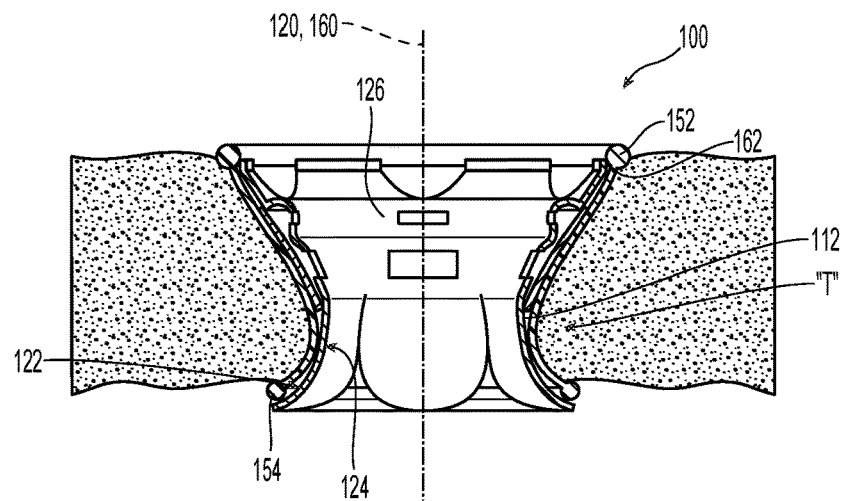
FIG. 1B is a cross-sectional view of the prior art system of FIG. 1A disposed within an opening in tissue.

Turning to FIGS. 1A and 1B, a prior art system 100 provided in accordance with the present disclosure includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 152 distally about body 156, to retract tissue "T" and/or secure access device 150 within the opening in tissue "T." Access device 150 may further define an inwardly-extending overhang 162 between proximal rim 152 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Figure 1C:
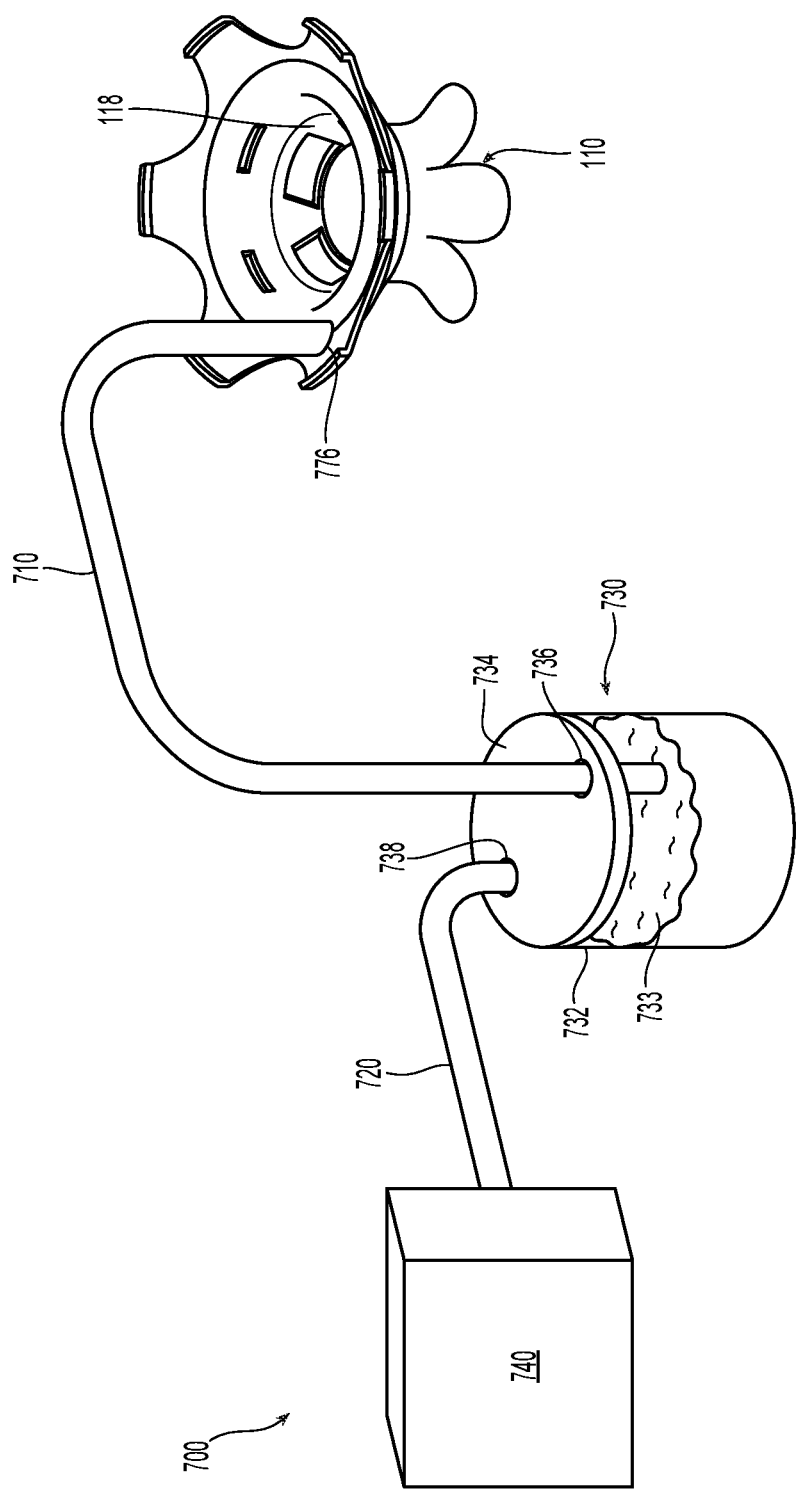
FIG. 1C is a schematic illustration of a smoke evacuation system for use with one or more of the access devices and tissue guards described herein.

Turning to FIG. 1C, smoke evacuation system 700 is provided in accordance with the present disclosure and is shown generally including tissue guard 110, tubing 710, 720, a collection reservoir 730, and a smoke evacuation (or vacuum) source 740. The various tissue guards disclosed herein are all designed to work with system 700. Tissue guard 110 and tubing 710 are detailed above and are coupled to one another, e.g., via engagement of one end of tubing 710 about exhaust connection 776 of tissue guard 710. The other end of tubing 710 extends into collection reservoir 730 in sealing relation therewith.

Collection reservoir 730 includes a base 732 and a lid 734 sealed about base 732. Lid 734 defines first and second ports 736, 738 configured to receive ends of tubing 710, 720, respectively, in sealing relation therewith. These ends of tubing 710, 720 extend into the interior volume 733 of base 732 and are spaced-apart from one another as well as the bottom of base 732. Tubing 720 extends from collection reservoir 730 to smoke evacuation source 740 wherein the other end of tubing 720 is coupled to smoke evacuation source 740. In this manner, upon activation of smoke evacuation source 740, suction is established through lip 126 of tissue guard 110, tubing 710, collection reservoir 730, tubing 720, to smoke evacuation source 740. During use, this suction, in addition to evacuating smoke from tissue guard 110, may also suction liquids, tissue, and/or debris through tubing 710. However, as a result of the ends of tubing 710, 720 being spaced-apart from one another within collection reservoir 730 and spaced-apart from the bottom of base 732 of collection reservoir 730, the liquids, tissue, and/or debris are suctioned into collection reservoir 730 and deposited therein, while only the smoke and other gaseous fluids are further suctioned from collection reservoir 730 through tubing 720 to smoke evacuation source 740. As such, smoke evacuation source 740 is protected by inhibiting suctioning of liquids, tissue, and/or debris into smoke evacuation source 740.

Figure 2A:
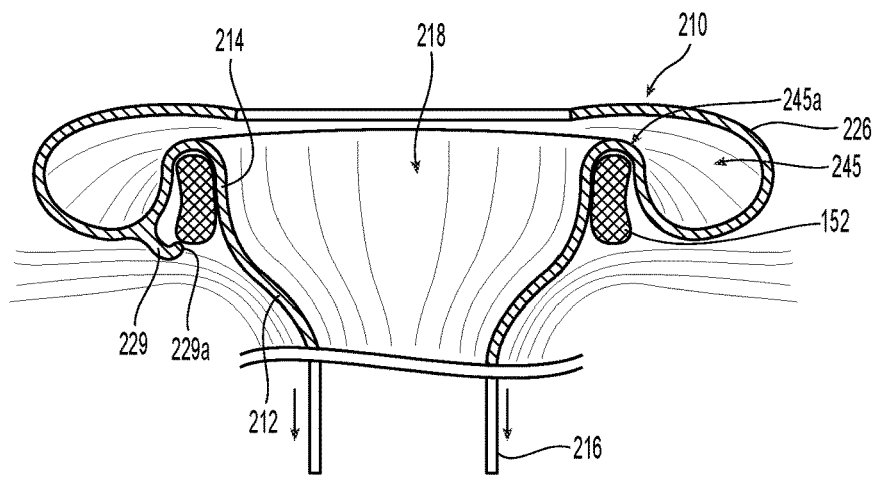
FIG. 2A is a side cross sectional view of a tissue guard for use with the access device.
Figure 2B:
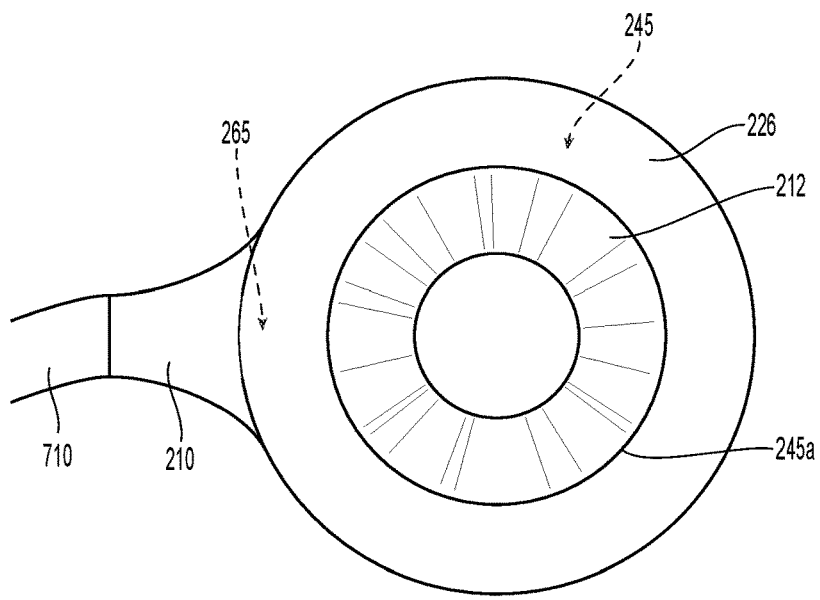
FIG. 2B is a top view of the tissue guard of FIG. 2A showing a smoke evacuation port connection.

Turning to FIGS. 2A-2B, a tissue guard 210 provided in accordance with the present disclosure is shown. Tissue guard 210 is similar to tissue guard 110 except as explicitly contradicted below and may be used in conjunction with access device 150 as part of a system similar to system 100. For purposes of brevity, only differences between tissue guard 210 and tissue guard 110 are detailed below, while similarities are summarily described or omitted.

Tissue guard 210 includes a body 212 defining an open proximal end 214, an open distal end 216, and a lumen 218 extending therebetween. An annular lip 226 extends radially outwardly from open proximal end 214 of body 212 and includes a plurality of fingers 229 extending from an outer peripheral surface thereof. The fingers 229 may be equidistantly-spaced about the lip 226 or may be spaced in any particular manner depending upon a particular purpose. In embodiments, a continuous finger (not shown) may be annularly spaced about the lip 226.

Each finger 229 extends from an inner peripheral surface of lip 226 to engage an underside of rim 152 of access device 150. Each finger 229 also includes a flange 229a configured to engage the underside of rim 152 to secure the tissue guard 210 in place. Finger 229 is configured to flex upon adaption of the tissue guard 210 onto access device 150 by virtue of rim 152 forcing flange 229a and finger 229 outwardly as the finger 229 is wedged under rim 152. Upon full insertion of the tissue guard 210 atop and into access device 150, the flange 229a snaps into place under rim 152 thereby locking the tissue guard 210 atop access device 150. The flange 229a is biased in the engaged position. Flange 229a may be angled or include angled surfaces to both facilitate insertion and to facilitate engagement.

The distal end 216 of tissue guard 210 may include a plurality of scallop-like tabs spaced-apart annularly thereabout that are configured engage an inner peripheral surface of body 112 of the access device 150 and are contoured or scalloped to generally mimic the shape thereof. The scallop-like tabs may be biased outwardly to maximize the opening at the distal end 216 of the tissue guard 210 and effectively secure the distal end 216 of the tissue guard 210 within access device 150 thereby facilitating surgical instrument access to the body cavity.

Lip 226 defines an annular channel 245 therein configured to direct surgical exhaust therethrough to port 265 defined in an outer peripheral surface of lip 226 which, ultimately, connects to a smoke evacuation connection 210. Annular channel 245 of lip 226 is configured in fluid communication with lumen 218 to direct surgical exhaust gases from lumen to the smoke evacuation system 700 through connection 210. Lip 226 also includes a substantially bulbous cross section to encourage engagement with rim 152 of access device 150 when tissue guard 210 is placed thereatop.

Annular channel 245 includes a narrowed channel or neck 245a disposed at the junction between the lumen 218 and lip 226. Neck 245a is configured to provide a Venturi Effect to the surgical gases exiting the lumen 218. In other words, the neck 245a may be configured to utilize the unique principles taken from the Venturi Flow Equation to maximize the air evacuated from the surgical cavity while minimizing the noise produced via turbulence. The neck 245a may be configured with specific ratios of cross sectional area to maximize the gas a and smoke evacuation through the neck 245a and into the annular channel and, ultimately, through the connection 210 to the smoke evacuation system 700. As mentioned above, necks with geometry to induce a Venturi Effect may be employed along with other geometries that may produce other desired effects, e.g., vortex-style effects.

Further, the neck 245a may prevent smoke accumulation in a specimen bag as well as above the surgical site by evacuating smoke from both areas. Details relating to tissue guards utilizing various smoke evacuation effects such as the Venturi Effect are described in commonly-owned U.S. application Ser. No. 16/750,150 filed on Jan. 23, 2020 the entire contents of which being incorporated by reference herein.

Figure 3:
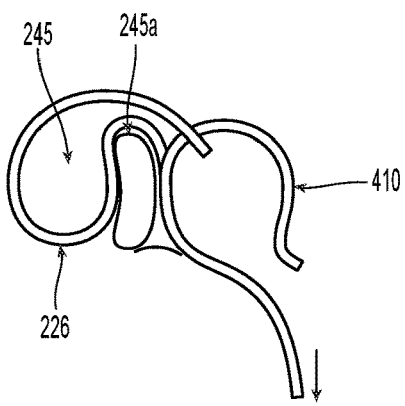
FIG. 3 is a side view of another one embodiment of a tissue guard for use with the access device in accordance with the present disclosure shown superimposed with a prior art design.

Connection 210 projects from lip 226 (in fluid communication with annular channel 245) laterally or generally perpendicular to an axis defined through lumen 218 to facilitate engagement with tubing 710 of the smoke evacuation system 700. In other words, the connection 210 sits generally flush with the surrounding geometry of the access device 150 and tissue guard 210. The tubing 710, in turn, does not interfere with access to the surgical site. Configuring the connection 210 in this fashion also provides a lower profile to the overall tissue guard 210 and increases visibility of the surgical site as best shown in FIG. 3. In other words, incorporating the lip 226 and smoke evacuation connections, e.g., connection 210 and tubing 710, on the outer periphery of the lip 226 which is, in turn, disposed on the outside of the rim 152 of access device 150, provides better access for the surgeon to the operating site. For example, FIG. 3 shows a typical arrangement of a prior art tissue guard 410 superimposed with the presently-disclosed tissue guard 210 illustrating this purpose.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard for use with a surgical access device, comprising:
   a body including a proximal end, a distal end and a lumen defined therebetween;
   a proximal lip extending radially from the proximal end and configured to mount atop a rim of an access device;
   a neck disposed at a junction between the lumen and the proximal lip, the neck monolithically forming a narrowed channel extending along a circumference of the proximal end of the body;
   an annular channel defined in the proximal lip and disposed in fluid communication with the lumen through the neck, the annular channel configured to direct surgical gases from the lumen, through the neck, and to a smoke evacuation system, the neck including geometry configured to induce the evacuation of surgical gases from the lumen to the annular channel of the proximal lip, wherein the proximal lip is an uninterrupted extension of the body to create an uninterrupted flow of surgical gases from the lumen through the neck and to the annular channel along an internal surface of the body to an internal surface of the proximal lip; and
   at least one finger extending from the proximal lip and configured to engage an access device to secure the tissue guard thereon.

2. The tissue guard according to claim 1, wherein the proximal lip is bulbous to encourage engagement with the rim of the access device.

3. The tissue guard according to claim 1, wherein the finger includes a flange configured to engage an underside of the rim of the access device to facilitate engagement therewith.

4. The tissue guard according to claim 3, wherein the finger is biased in an engaged configuration.

5. The tissue guard according to claim 1, wherein the proximal lip includes a connection disposed in fluid communication with the annular channel and extending perpendicularly from the proximal lip.

6. The tissue guard according to claim 5, wherein the connection sits flush with the access device.

7. The tissue guard according to claim 1, wherein the geometry of the neck induces a Venturi Effect from the lumen to the annular channel.

8. The tissue guard according to claim 1, wherein the geometry of the neck induces a vortex effect from the lumen to the annular channel.

9. The tissue guard according to claim 1, wherein the geometry of the neck is configured to maximize the flow of surgical gases therethrough.

10. A tissue guard for use with a surgical access device, comprising:
    a body including a proximal end, a distal end and a lumen defined therebetween; and
    a proximal lip extending radially from the proximal end and configured to mount atop a rim of an access device;
    a neck disposed at a junction between the lumen and the proximal lip and monolithically forming a narrowed channel extending along a circumference of the proximal end of the body; and
    an annular channel defined in the proximal lip and disposed in fluid communication with the lumen through the neck, the annular channel configured to direct surgical gases from the lumen, through the neck, and to a smoke evacuation system, the neck including geometry configured to induce the evacuation of surgical gases from the lumen to the annular channel of the proximal lip, wherein the proximal lip is an uninterrupted extension of the body to create an uninterrupted flow of surgical gases from the lumen through the neck and to the annular channel along an internal surface of the body to an internal surface of the proximal lip.

11. The tissue guard according to claim 10, wherein the proximal lip is bulbous to encourage engagement with the rim of the access device.

12. The tissue guard according to claim 10, wherein the proximal lip includes a connection disposed in fluid communication with the annular channel and extending perpendicularly from the proximal lip.

13. The tissue guard according to claim 12, wherein the connection sits flush with the access device.

14. The tissue guard according to claim 10, wherein the geometry of the neck induces a Venturi Effect from the lumen to the annular channel.

15. The tissue guard according to claim 10, wherein the geometry of the neck induces a vortex effect from the lumen to the annular channel.

16. The tissue guard according to claim 10, wherein the geometry of the neck is configured to maximize the flow of surgical gases therethrough.

17. A tissue guard for use with a surgical access device, comprising:
   a body including a proximal end, a distal end and a lumen defined therebetween; and
   a proximal lip extending radially from the proximal end and configured to mount atop a rim of an access device;
   a neck disposed at a junction between the lumen and the proximal lip and monolithically forming a narrowed channel extending along a circumference of the proximal end of the body; and
   an annular channel defined in the proximal lip and disposed in fluid communication with the lumen through the neck, the annular channel configured to direct surgical gases from the lumen, through the neck, and to a smoke evacuation system, the neck including geometry configured to induce a Venturi Effect from the lumen to the annular channel or induce a vortex effect from the lumen to the annular channel, wherein the proximal lip is an uninterrupted extension of the body to create an uninterrupted flow of surgical gases from the lumen through the neck and to the annular channel along an internal surface of the body to an internal surface of the proximal lip.

18. The tissue guard according to claim 17, further comprising at least one finger extending from the proximal lip and configured to engage an access device to secure the tissue guard thereon, wherein the finger includes a flange configured to engage an underside of a rim of the access device to facilitate engagement therewith.

19. The tissue guard according to claim 18, wherein the finger is biased in an engaged configuration.

20. The tissue guard according to claim 17, wherein the proximal lip is bulbous to encourage engagement with the rim of the access device.

* * * * *